United States Patent [19]

Bielka

[11] 4,206,766

[45] Jun. 10, 1980

[54] APPARATUS FOR DETECTING ANIMAL ESTRUS

[76] Inventor: Robert P. Bielka, 2211 N. 59th St., Seattle, Wash. 98103

[21] Appl. No.: 928,829

[22] Filed: Jul. 28, 1978

[51] Int. Cl.[2] ........................ A01K 11/00; A61B 10/00

[52] U.S. Cl. .......................................... 128/738; 119/1

[58] Field of Search .................... 128/738; 119/1, 109, 119/159

[56] References Cited

U.S. PATENT DOCUMENTS

| | | | |
|---|---|---|---|
| 3,076,431 | 2/1963 | Rule et al. | 128/738 |
| 3,158,133 | 11/1964 | Larson | 128/738 |
| 3,824,989 | 7/1974 | Horner et al. | 128/738 |
| 3,842,802 | 10/1974 | Lang et al. | 128/738 |

*Primary Examiner*—Willis Little

*Attorney, Agent, or Firm*—Graybeal & Uhlir

[57] ABSTRACT

An animal estrus detection apparatus adapted to be secured to the rump portion of a first animal, and actuated by a second animal mounting the first and thereby applying a predetermined amount of pressure thereon a depressible pin. The pin's motion is transferred by a linkage mechanism to a release mechanism, which then disengages an outer cover causing it to fall away and deploy an estrus indicating streamer. The release mechanism may include either a pneumatic or an escapement type release timer which is powered by said linkage and which prevents said linkage from powering said release mechanism until a predetermined period of time has elapsed. The release mechanism may also include a counting mechanism which actuates the release arm only after a predetermined number of successive mountings of said first animal. A second, hydraulic timer, actuated when the outer cover is released, measures the time elapsed since the outer cover's release.

15 Claims, 11 Drawing Figures

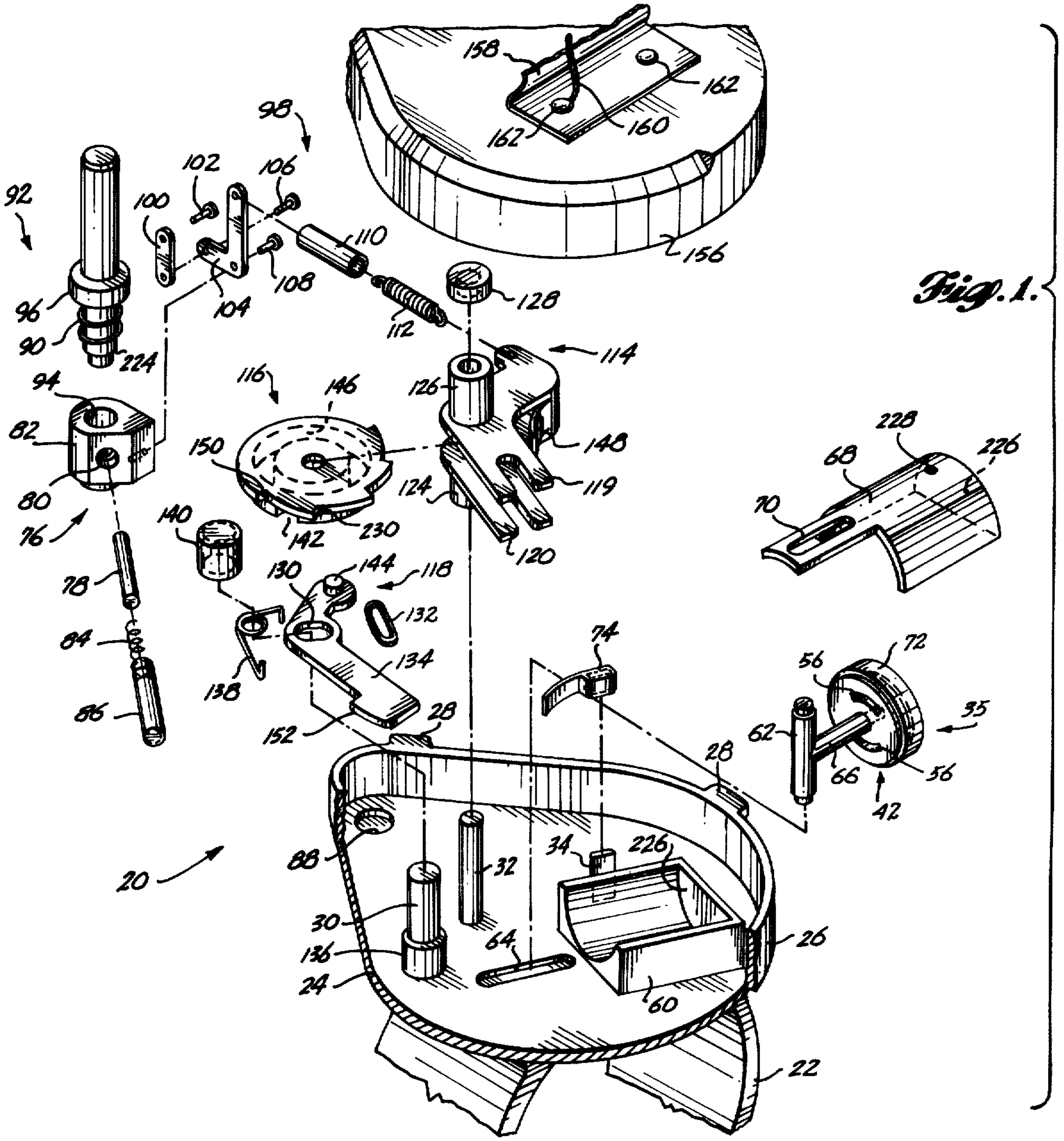
Fig. 1.
Fig. 2.
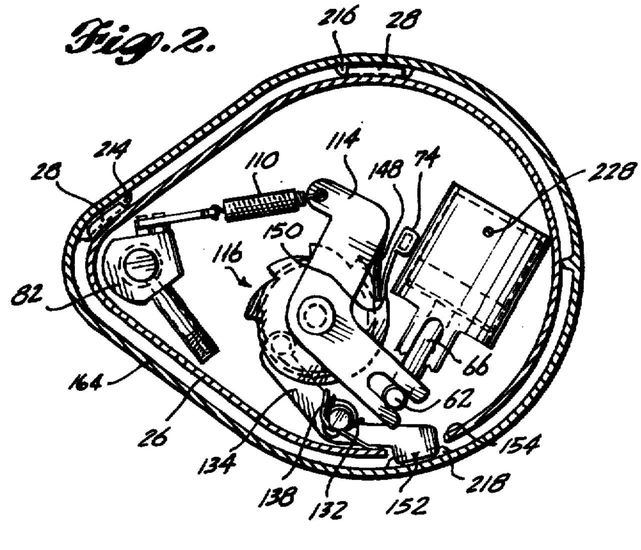
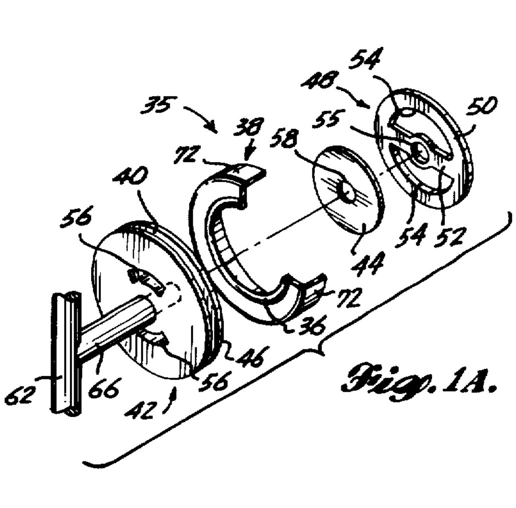
Fig. 1A.

APPARATUS FOR DETECTING ANIMAL ESTRUS

BACKGROUND OF THE INVENTION

1. Field of the Invention

This invention relates to apparatus used to detect animal estrus, and more particularly to such apparatus which is adapted to be worn externally by a first animal and is pressure actuated by a second animal mounting the first animal.

2. Description of the Prior Art

In the field of animal husbandry, mankind is continually seeking to improve his livestock by the selective breeding thereof. However, such breeding entails determination of when estrus is occurring in the livestock so that, to the greatest extent possible, the livestock can be impregnated through the selective utilization of the preferred source of natural or artificial insemination.

As is known, estrus is characterized by an increase in the mucus present in the vaginal canal of an animal. Thus, prior art patents such as U.S. Pat. No. 3,297,020 granted Jan. 10, 1967, to Mathiesen, and U.S. Pat. No. 3,844,276 granted Oct. 29, 1974, to McDougall, disclose apparatus which includes a probe insertable into the vaginal canal for detecting either an increase in current flow through the mucus or a decrease in the resistance of the mucus, respectively, which indicates the animal is in estrus.

As is also known, when estrus occurs in livestock, such as a cow for example, the cow will show an increased tendency to stand and permit itself to be mounted by other animals. When the mounted animal allows the mounting animal to remain for about five seconds, a "standing mount" has occurred. The most frequent mountings occur, of course, by bulls, but mountings are also made by other cows. Accordingly, the repeated mounting of a cow by any other such animal is a good indication that it is in estrus. The occurrence of a number of "standing mounts" indicates true estrus and the optimum time for artificial insemination is immediately following occurrence of the fifth standing mount, according to experts in the field. The time elapsed since the fifth standing mount is grossly indicative of the number of artificial insemination ampules required to ensure fertilization of the cow.

Although throughout this application a cow is used as an example, it is to be understood that the present invention may be easily adapted to be used to detect estrus in other animals such as horses, sheep, goats, swine, etc.

Some of the prior art patents, such as U.S. Pat. No. 3,842,802, granted Oct. 22, 1974, to Lang et al., and U.S. Pat. No. 3,824,989, granted July 23, 1974. to Horner et al., take advantage of the aforesaid behavior by attaching to the bull's head or neck a harness which carries a marking device arranged to mark the cow when the bull mounts the cow, thereby indicating the presence of estrus in that cow. However, such devices suffer from the drawbacks that they are relatively expensive and complicated. In addition, it would appear that they are not too useful for selective breeding purposes since the marking animal, the bull, has likely already inseminated the cow in the process of marking it unless the bull has been surgically rendered incapable of inseminating the cow.

U.S. Pat. No. 3,844,273, granted Oct. 29, 1974, to Polson discloses an apparatus which includes a battery operated radio transmitter worn by each cow. The transmitter is turned on when the cow is mounted by another animal, thereby indicating the presence of estrus to the animal breeder who may then locate the cow by utilizing a radio direction finder. Polson also discloses electrical means to measure the amount of time elapsed since the radio transmitter is turned on. However, the Polson apparatus suffers from the drawbacks of being relatively expensive, hard to repair, and having a relatively limited range. In addition, it would seem that the Polson apparatus would be subject to being unable to perform its intended function relatively frequently in the event that batteries become old and fail or in the event the batteries become discharged after the transmitter has been activated for a period of time before the animal breeder can locate that particular cow. Further, it indicates only that at least one mount has occurred and does not indicate the number of mounts or the length of any.

U.S. Pat. No. 3,076,431, granted Feb. 5, 1963, to Rule et al., and Canadian counterpart application Ser. No. 682,861, granted Mar. 24, 1964, disclose a pressure activated, hydraulic type of estrus detection device which is secured to the rump of a cow. This device is in the form of a long tube divided into two interconnected compartments, one compartment being soft walled and partially filled with a colored fluid, while the other compartment has collapse resistant walls and includes an aperture leading to an absorbent material which surrounds the tube. Pressure on the device caused by another animal forces the colored fluid into the collapse resistant compartment and thence into the absorbent material, thereby indicating the presence of estrus. The time taken to fill the collapse resistant compartment with fluid is alleged in the Rule patent to act as a mechanism whereby short applications of pressure on the tube will not give an observable indication of colored fluid on the absorbent material, although applicant doubts the consistant operability of this aspect of the Rule disclosure. However, as will be seen, the Rule device utilizes a construction and operating principle quite different from that disclosed by applicant. Further, it does not count the mounts and does require close observation of the animal's rump area.

SUMMARY OF THE INVENTION

As has been mentioned, the apparatus of the present invention is adapted to be secured to the rump portion of the first animal. In basic form, it includes a pressure responsive means connected to an indicating means to thereby indicate the presence of estrus in the first animal. By thus providing that at least a predetermined pressure must be exerted on the pressure responsive means prior to the release of the release means, the applicant is able to achieve one of the objects of the present invention, which is to prevent spurious releases of the indicating means caused by pressures on the pressure responsive means which are less than those occurring during an actual mounting, such as those caused by a second animal resting its head on the apparatus of the present invention.

In some aspects of the present invention, said predetermined pressure is determined by specifying the pressure responsive means to include a pressure regulatory means. The regulatory means may be specified to simply be a spring which prevents depression of said pressure responsive means until it is subjected to said predetermined pressure. Alternatively, the pressure responsive means may include a depressible member, and the pressure regulatory means may include a housing which receives one end of a length of relatively soft material as well as one end of the depressible member. The housing is so arranged that the depressible member must sever a piece of said material before the member can be substantially depressed, thereby preventing substantial movement of said depressible member until it is subjected to at least said predetermined pressure.

Another aspect of the present invention specifies the release means to include a release timing means for preventing said movable release member from releasing the indicating means until said release timing means has been powered by said linkage means for at least a predetermined period of time. This construction helps applicant to achieve another objective of the present invention which is to prevent spurious releases of the indicating means caused by pressure on the pressure responsive means which is not of a sufficient duration to reliably indicate that an effective mounting of the first animal by the second animal has occurred.

In other aspects of the present invention, the release timing means may comprise either an escapement mechanism or a timing piston and an associated timing cylinder. The latter apparatus determines the aforesaid predetermined period of time by the length of time it takes the timing piston to move a predetermined distance under the urging of the linkage means.

Another object of the present invention is to provide an animal estrus detection apparatus which releases the indicating means only after a predetermined number of mountings of the first animal have taken place. This is desirable information because the stock breeder may want to artificially inseminate the cow only after a predetermined number of mountings, felt sufficient to indicate the cow is in estrus, have occured. If said predetermined number of mountings is set at greater than one, the foregoing object of the present invention also serves to reduce the occurrence of spurious releases of the visual indicator caused by the isolated happenchance mounting of a cow by another animal, which may occur even though the cow is not in estrus. Thus, the present invention avoids some of the drawbacks of the prior art which indicate that the animal is in estrus after only one mounting of the cow wearing the detection apparatus.

The present invention achieves the foregoing object by providing a counting mechanism which actuates the movable release member, thereby releasing the indicating means, only when the counting mechanism is advanced a predetermined number of times. Of course, the counting mechanism is advanced one count each time the pressure responsive means is subjected to at least said predetermined pressure caused by the mounting of said first animal, and, if a release timing means is utilized, the counting mechanism will not be advanced until said predetermined pressure is exerted for at least a predetermined period of time.

Other aspects of the present invention specify the counting mechanism to include a ratchet wheel means which defines a circular slot having a release slot. One end of said movable release member rides in the circular slot and is released through the release slot only after the ratchet wheel means has been advanced said predetermineed number of counts.

A further object of the present invention is to provide a mechanism for indicating the amount of time that has elapsed since the indicating means has been released. This is important since, as is known, the duration of estrus in a cow is for a relatively short period of time.

Thus, if release of the indicating means is taken to approximate the start of estrus, then an apparatus for indicating the elapsed time since release helps the stock breeder to determine whether or not the most favorable time for inseminating that cow has passed.

The foregoing object is achieved by some aspects of the present invention which specify the indicating means to include an elapsed time timing means which indicates the amount of time that has elapsed since the indicating means has been released. The elapsed time timing means may be specified to comprise a chamber enclosing a quantity of fluid wherein, after the indicating means is released, the fluid is allowed to escape from the chamber through a small aperture at a predetermined rate. As the fluid is released, an elapsed time exhibiting means is exposed in an amount proportional to the amount of fluid released through the small aperture.

A further object of the present invention is to provide an apparatus which achieves the foregoing objectives while still being simple, durable, reliable, and so inexpensive that it can be thrown away after one use.

These and further objects, features, advantages and characteristics of the animal estrus detection apparatus of the present invention will be apparent from the following more detailed description of the preferred embodiments.

BRIEF DESCRIPTION OF THE DRAWINGS

FIG. 1 is an exploded isometric view, from an upper aspect, of portions of the animal estrus detection apparatus of the present invention;

FIG. 1A is an exploded isometric view, from an upper aspect, specifically illustrating the construction of the release timing mechanism utilized in FIG. 1;

FIG. 2 is a transverse cross section of the apparatus shown in FIG. 1 when assembled;

DESCRIPTION OF THE PREFERRED EMBODIMENTS

Figure 3:
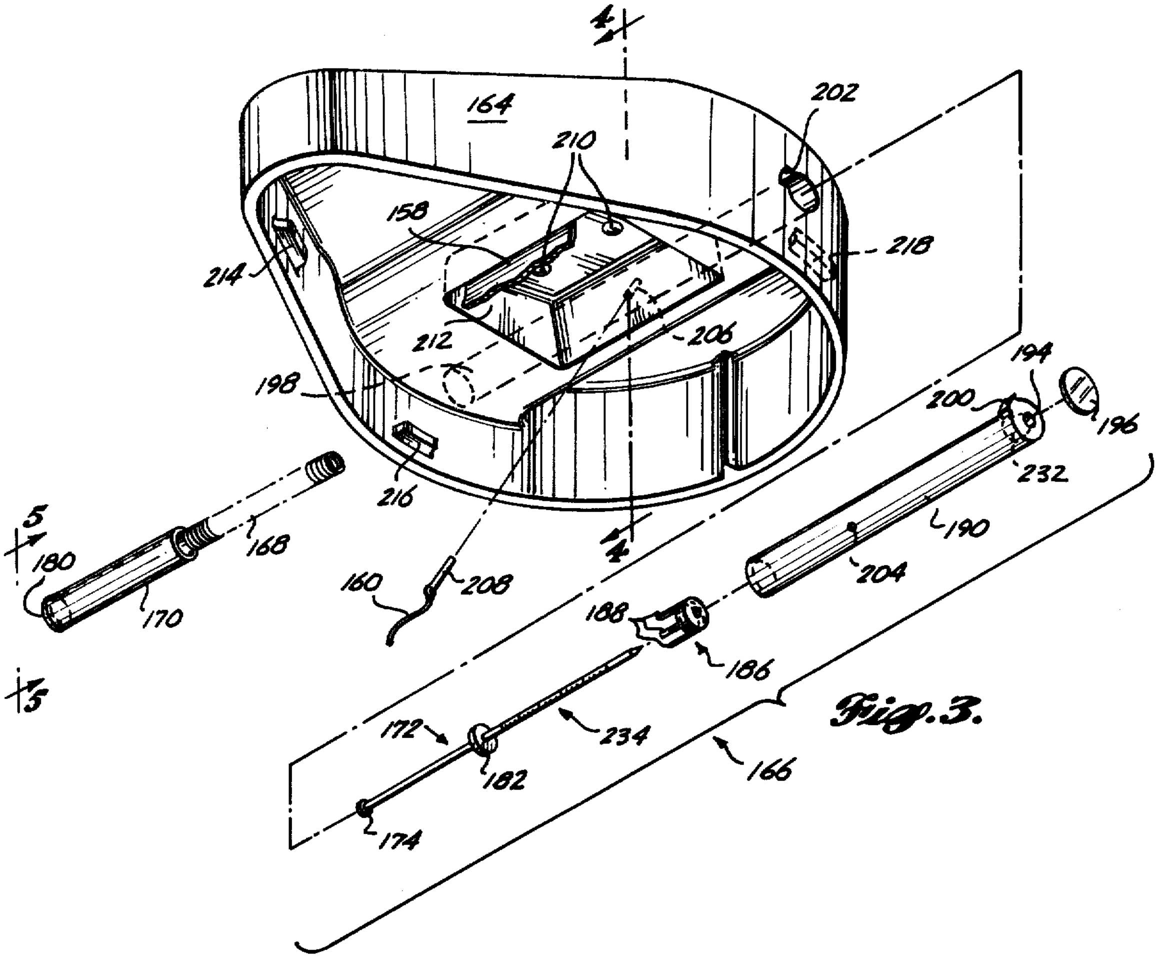
FIG. 3 is an exploded isometric view from a lower aspect of the outer cap and elapsed time indicating mechanism of the present invention.

Assembly and construction of the embodiment of the animal estrus indicating apparatus 20 of the present invention shown in FIGS. 1-6 will be considered first. Referring now to FIG. 1, the apparatus 20 is shown in an exploded view for clarity to aid in understanding the construction of the present invention. The apparatus includes a broad, circular attachment device 22 which is used to secure the apparatus to the tail of the cow, by inserting the tail therethrough or wrapping around the base of the tail a strap incorporating a suitably shaped enlargement molded to fit the pocket beneath the base of the tail and above the anus. This pocket is often referred to as the caudal fold. To the top of the attachment ring is secured, as by gluing or molding in one piece, a base housing 24 which includes a peripheral upstanding base wall 26 having a pair of latching ears 28 as shown. First, second and third upstanding posts 30, 32, 34 are secured to the base housing, as by gluing or molding in one piece with the housing.

Additionally referring to FIG. 1A, next a release timing mechanism 35, is assembled by first snapping the thickened rim 36 of a thin rubber cup seal 38 over the peripheral groove 40 in a timing piston 42. The center pin 66 extends through the hole 58 in the thin rubber check valve disc 44, which is secured to the end face 46 of the piston by a retaining washer 48. Washer 48 has a periphery 50 and a central cross bar 52, and is secured to said end face 46 by friction of the center pin 66 in the hole 55. The rubber disc 44 is sized so as to cover the check valve holes 56 in the piston 42, while holes 54 in the retaining washer are sized to permit flexing of said upper and lower portions of the rubber disc 44 therethrough. The center pin 66 prevents lateral movement of the disc.

Next, the assembled timing piston 42 is placed in the lower timing cylinder half 60, which is secured to the base housing 24, as by gluing or molding in one piece. The lower end of the transverse guide pin 62 is placed in the oval recess 64 in the base housing and is secured to the piston 42 by a lateral arm 66, with elements 42, 62, 66 being secured together, as by gluing or molding in one piece. Finally, the upper timing cylinder half 68 is secured to the lower cylinder half, as by gluing, with the upper end of the transverse guide pin 62 riding in the oval hole 70 in the upper cylinder half. It is understood that the large rim 72 of the cup seal 38 makes a snug, sealing, sliding contact with the upper and lower timing cylinder halves.

Next, a no-back pawl 74 is secured to the third post 34, as by a snug friction fit.

Then, a metal depressible pin spring 90 is inserted over the lower portion of a pressure responsive, metal depressible pin 92, as shown, and the lower end of the depressible pin is inserted into a main cavity 94 in the housing 82, with the spring 90 being compressed between the top of the housing 82 and a collar 96 on the depressible pin.

Next, a linkage mechanism 98 is assembled by securing a first link 100 to the annular collar 96 with a metal first link fastener 102. Then, the first link and a second link 104 are secured together by a metal second link fastener 106, while the second link is secured to the housing 82 by a metal third link fastener 108. A link spring housing 110 is passed over a metal link spring 112 and one end of the link spring is hooked through the hole in the top of the second link 104, as shown, while the other end of the link spring is hooked into a hole on one end of the link arm 114. A pressure regulatory mechanism 76 is then assembled by first inserting a length of detent material 78 into a side cavity 80 in pressure regulatory housing 82. Then a detent spring 84 is inserted into a tubular detent housing 86, which is then urged towards the detent material, thereby compressing the spring 84 between the detent material and the detent housing. The detent housing is secured, as by a threaded connection, or friction fit to the pressure regulatory housing, which is then affixed to a recess 88 in the base housing, as by gluing. It is understood that said main and side cavities 94, 80 are in communication, and that the detent spring 84 urges the detent material 78 into the main cavity beneath the bottom of the depressible pin 92 prior to said pin being fully depressed.

Next, a counting ratchet wheel 116, which forms part of a release mechanism 118, is inserted between the top and bottom extensions 119, 120 of a link arm 114, and the arm is passed down over the second post 32, which passes upwardly through a bottom collar 124, the bottom extension, the ratchet wheel, the top extension and a top collar 126 on the arm, and acts as a pivot for the ratchet wheel 116 and the arm 114. Finally, a cap 128 is pressed over the top of the second post with a snug friction fit.

Then, the bottom loop of a rubber elastic member 132 is passed down over the first post 30, the oval hole 130 in the movable release arm 134 is passed down over the post, so that the release arm is adjacent the top of the collar 136 on the post, and then the top loop of the elastic member is passed over the post in a position adjacent the top surface of the release arm. The loop in a metal release arm spring 138 is placed over the first post 30 adjacent the top loop of the elastic member and one end of release arm spring is hooked over the release arm, while the other end presses against the base wall 26, as shown in FIG. 2. Finally, a cap 140 is pressed with a snug friction fit over the post 30.

Next, the release arm is cocked by rotating the ratchet wheel 116 on the second post 32 so that its release slot 142 is adjacent the upwardly projecting pin 144 on one end of the movable release arm 134. The release arm is then manually rotated clockwise against the urging of the spring 138, about the first post 30, so as to pass said pin 144 through the release slot into a circular slot 146 in the ratchet wheel, and the ratchet wheel is manually rotated clockwise to thereby entrap the pin within the circular slot. The ratchet wheel's clockwise rotation is continued until the no-back pawl 74 and the advance pawl 148 on the link arm engage the first tooth 150 on the ratchet wheel. As seen in FIG. 2, at this time the dog 152 on the release arm extends through a release arm opening 154 in the base wall, the elastic member 132 urges the release arm into the position relative to said first post 30, as shown, and the spring 138 urges the release arm to rotate counterclockwise about the first post, said rotation being prevented by the entrapment of said pin 144 on the ratchet wheel's circular slot 146.

Next, a inner cap 156 is secured, as by gluing, to the base wall 26 and one end of the estrus and then indicating streamer 158 and one end of the lanyard 160 are connected to the top of the inner cap, as by fasteners 162.

Figure 5:
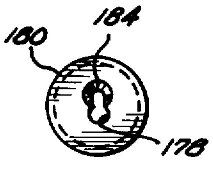
FIG. 5 is a plan view of a portion of the present invention shown in FIG. 3, taken along line 5—5 thereof.
Figure 6:
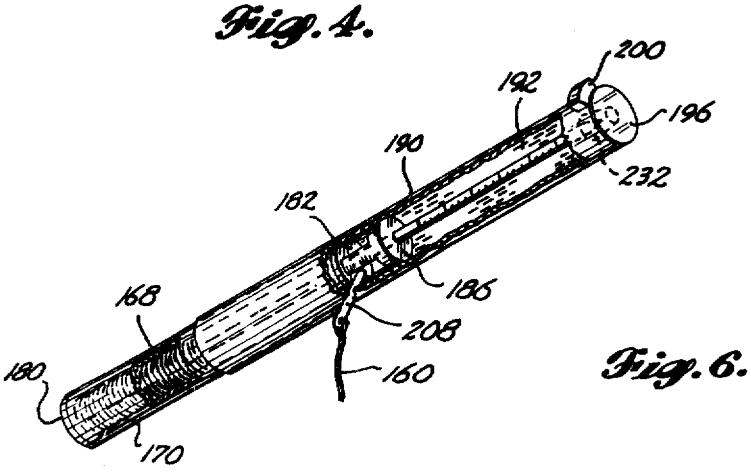
FIG. 6 is a transverse cross section of an elapsed time timing mechanism of the present invention when assembled.
Figures 7, 8:
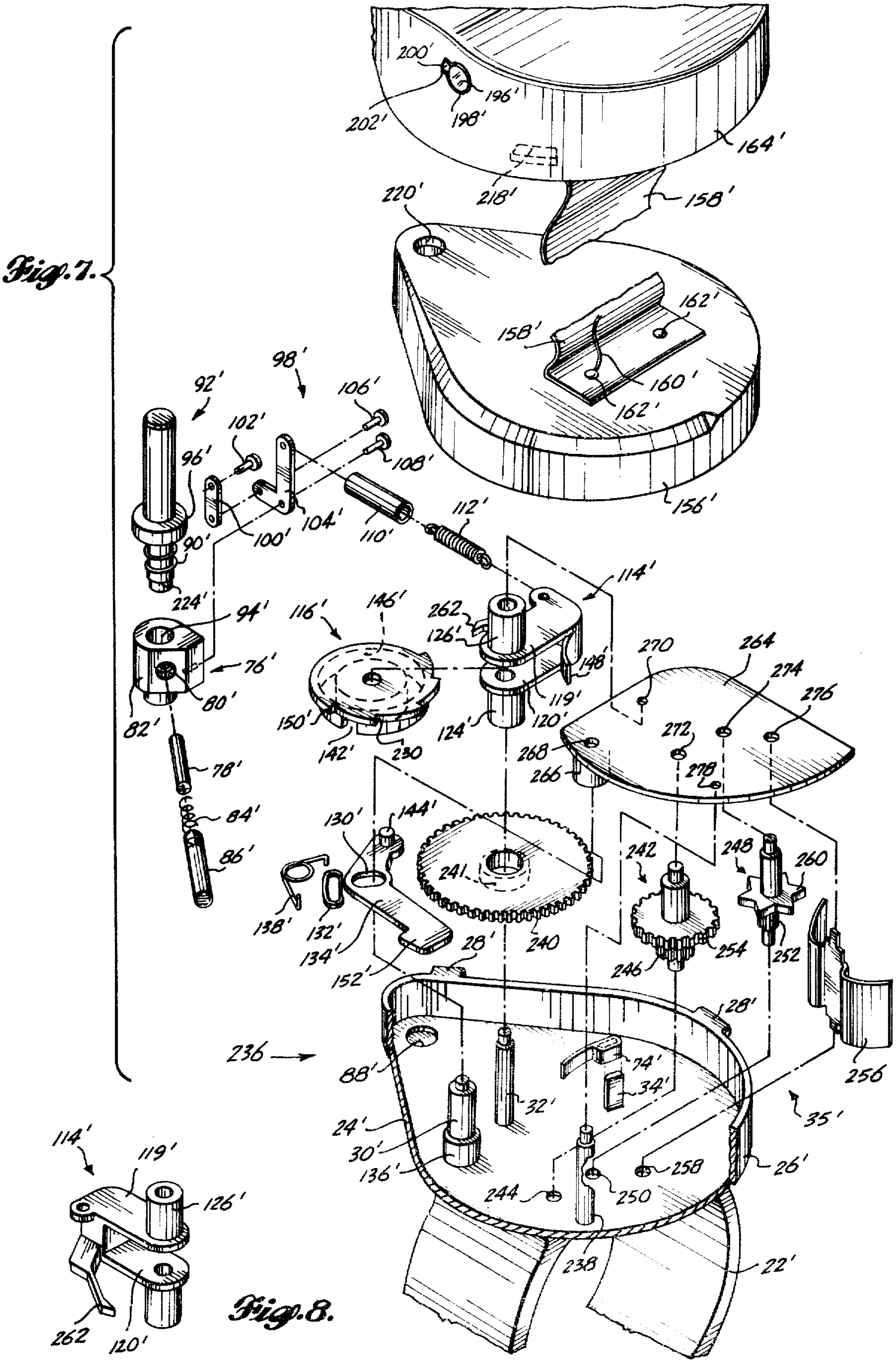
FIG. 7 is an exploded isometric view from an upper aspect of another embodiment of the present invention.
FIG. 8 is a view from the hidden side of one of the components of the present invention shown in FIG. 7.

The indicating mechanism, in the form of elements 158, 160 and the outer cap 164, includes an elapsed time indicating mechanism 166, shown in FIGS. 3, 5, and 6, which is assembled by first placing a metal spring 168 and a spacer 170 over one end of an elapsed time exhibiting shaft 172, said shaft 172 being metal or plastic. The head 174 on the shaft is inserted through the keyhole 178 in the end cap 180, thereby compressing the spring 168 between the cap 180 and the collar 182 on the shaft 172. The head is then raised upwardly in the keyhold 178 such that it rests in the depression 184 in the end cap, seen in FIG. 5, to thereby lock the spring 168 compressed between the cap 180 and the collar 182. Next a seal 186 is placed over the shaft 172 so that its legs 188 are adjacent the collar 182, and then the assembled shaft, spring 168, spacer 170, end cap 180 and seal are inserted into a sleeve 190 in the position shown in FIG. 6. Then the end cap 180 is glued to the end of the sleeve 190.

Then, as seen in FIG. 6, a quantity of viscous fluid 192, such as General Electric Company VISCASIL silicone type fluid is injected into the sleeve 190 through the small end hole 194, as by a hypodermic syringe, the quantity being sufficient to fill the cavity 196 between the seal 186 and the end hole, and an aluminum foil seal 196 is glued over the end hole. Next, the sleeve 190 and its contents are inserted into the transverse cavity 198 in the outer cap 164, with the key 200 on the sleeve resting in the keyhole recess 202 of said cavity to thereby align the release pin hole 204 in the sleeve and the release pin hole 206 in the outer cap.

The other end of the lanyard 160 is attached, as by gluing, to one end of the release pin 208 and the pin is inserted through the release pin holes 204, 206 in the outer cover and sleeve so that one end thereof protrudes into the sleeve 190 adjacent the collar 182. The elapsed time indicating mechanism 166 is then armed by releasing the head 174 through the larger opening of the keyhole 178 in the end cap so that the spring 168 urges the collar 182 on the shaft against the release pin 208.

Then, the end of the streamer 158 is connected to the outer cap, as by the fasteners 210. The lanyard is coiled in the generally square cavity 212 in the outer cap 164 and the streamer is tightly folded into said cavity 212. Referring now to FIG. 2, the outer cap is then secured to the base wall 26 by interlocking its first and second shelves 214, 216 with the latching ears 28 on the base wall, and the dog 152 on the release arm is manually moved through the release arm opening 154, so that the end of the dog 152 is adjacent the base wall 26. Then, the outer cap is pressed down, with the dog 152 springing outwardly, under the urging of the elastic member 132, over the third shelf 218 on the outer cap, thereby locking the outer cap to the base wall, while confining the streamer between the inner and outer caps.

Figure 4:
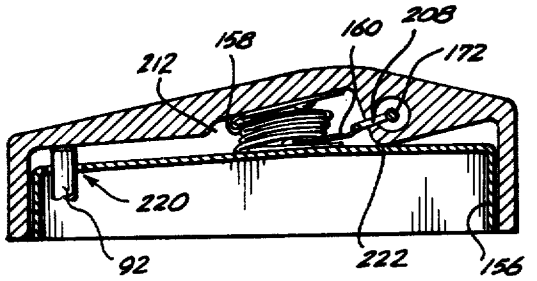
FIG. 4 is a transverse cross section of the apparatus shown in FIG. 3, when assembled, taken substantially along line 4—4 thereof with some elements omitted for clarity.

When the animal estrus indicating apparatus 20 is assembled, as shown in FIG. 4, the depressible pin 92 extends outwardly through the inner cap through the depressible pin hole 220 and abuts against the inner surface of the outer cap. As will be appreciated, all the parts of the embodiment of the animal estrus indicating apparatus 20, shown in FIGS. 1–6, may be formed, as by injection molding, from any strong, durable, rigid plastic such as polyallomer except, of course, for the parts whose composition has been previously indicated. The detent material is a relatively soft plastic such a polyethylene and the streamer is any brightly colored material, such as plastic or cloth.

Now that a description has been given of the construction and assembly of the animal estrus indicating apparatus 20 shown in FIGS. 1–6, an explanation of the operation of this apparatus will now be set forth. As was previously described, the release arm 134 has been cocked and the elapsed time timing apparatus 166 has been armed. It will be understood that the apparatus 20 is ready for operation when the various components thereof have been assembled in the relation shown in FIG. 2, with the advance pawl 148 and the no back pawl 74 engaging the first tooth 150 on the ratchet wheel 116.

Now, when the apparatus 20 has been secured to a first animal by attachment device 22, as previously described, with the broad end of the base housing 24 pointed rearwardly on the animal, the apparatus is ready to perform its intended function. Referring to FIG. 4, when a second animal mounts the first animal, the weight of the second animal on the outer cap 164 causes it to pivot on the inner cap 156 on the shoulder 222 of the outer cap. As the outer cap pivots, it exerts pressure on the pin 92, thereby depressing it and setting into motion the apparatus 20.

Referring now to FIGS. 1 and 2, as the depressible pin 92 is forced downwardly, the shoulder 224 on the lower end of the pin 92 is prevented by the detent material 78 beneath it from moving substantially downwardly until a pressure has been exerted on the depressible pin sufficient to sever the detent material. It will be appreciated that this provision of the detent material prevents inadvertent actuation of the apparatus 20 caused by pressures on the pin 92 less than those normally encountered by a mounting of the first animal by a second animal, such as those caused by a second animal resting its head on the apparatus 20. Of course, it is also understood that the detent material 78, the detent spring 84, the detent housing 86 and the side cavity 80 on the regulatory housing could be eliminated by merely making the spring 90 associated with the pin 92 sufficiently strong so that the pin cannot be urged downwardly through its full motion until a pressure is exerted on the pin which is equal to that needed to cause the pin to sever a small portion of said detent material.

As the depressible pin 92 moves downwardly after severing the detent material, its downward motion is transferred by the first and second links 100, 104 to the link spring 112, thereby stretching the spring and causing it to exert a tension on the link arm 114, causing the arm to rotate counterclockwise about the second post 32. The top and bottom extensions 119, 120 of the link arm, which engage the transverse guide pin 62 of the piston 42, urge the timing guide pin, and thus its associated timing piston 42, inwardly towards the end walls 226 of the upper and lower cylinder halves, thereby compressing the air trapped between said piston and said end walls. As seen, a small bleed hole 228 through which said air can escape is provided in the upper cylinder half, and it will be appreciated that the time taken for the link arm 114 to rotate enough to urge the piston through its full range of travel will depend upon the sizing of the bleed hole and the strength of the link spring 112. These components are sized so that full travel of the piston under the urging of the link arm will take about four seconds, for example, a time deemed sufficient to reliably indicate that a "standing mount" has taken place. Of course, the size of the bleed hole and the strength of the spring 112 could be selected differently to give a time shorter or longer than the four seconds mentioned.

It will be understood that, as the piston moves towards the end walls 226 under the urging of the link arm, a corresponding rotation of the link arm about the second post 32 occurs, so that only when the piston moves its full distance towards said end walls has the arm 114 rotated enough so that its advance pawl 148 will engage the second tooth 230 on the ratchet wheel. The no back pawl 74 prevents counterclockwise rotation of the ratchet wheel as the arm 114 and its advance pawl 148 are rotated counterclockwise. Of course, it is also to be understood that should the depressible pin 92 be subjected to said pressure for a time less than the four seconds it takes the link arm to urge the piston to travel its full distance towards the end walls, the link arm will not rotate a sufficient distance to engage the second tooth on the ratchet wheel, and thus the ratchet wheel will not count a mounting. Thus, it is seen that the release timing mechanism 35 prevents the advance pawl 148 of the linkage mechanism 98 from rotating the ratchet wheel 116 of the release mechanism 118 clockwise, to count a mounting and possibly actuating the release arm, as will be described, if the period of pressure on the depressible pin 92 is less than four seconds.

After the mounting has been terminated, the pressure on the outer cap 164 caused by the second animal is relieved and the depressible pin 92 is urged upwardly by its associated spring 90. As the lower end of the depressible pin clears the top of the side cavity 80, the detent spring 84 urges the detent material 78 from the side cavity into the main cavity 94 beneath the shoulder 224 of depressible pin 92. As the depressible pin moves upwardly, its motion is transferred through the first link 100, the second link 104 and the link spring housing 110 to the link arm, causing the link arm 114 to rotate clockwise about the second post 32. If the pressure on the depressible pin lasted four seconds or longer, and the advance pawl 148 engaged the second tooth 230 on the ratchet wheel, the advance pawl will then rotate the ratchet wheel clockwise, resulting in a configuration similar to that shown in FIG. 2, except that the advance pawl and the no-back pawl 74 would rest on the second tooth 230 of the ratchet wheel, and the ratchet wheel, by its rotation, has counted one mounting. Of course, for pressure of less than four seconds' duration on said depressible pin, the advance pawl 148 does not engage the second tooth of the ratchet wheel, and the advance pawl returns to its original position, shown in FIG. 2, on the first tooth 150 of the ratchet wheel.

As the link arm is rotating clockwise, it will be appreciated that it is urging the piston 42 away from the end walls 226 and returning the piston to its initial position, shown in FIG. 2. The motion of the piston as it returns to its original position is assisted by a check valve in the piston 42, comprising the check valve holes 56 and the rubber disc 44, which, in the usual fashion permits air to freely enter into the space between the piston and said end walls during the piston's return motion. Of course, when the piston was compressing the air during its travel towards said end walls, the rubber disc was forced tightly over the check valve holes preventing any leakage therethrough.

Subsequent mountings of the first animal result in operation of the apparatus 20 as has been heretofore described, except after each mounting of the required four seconds has occurred, the advance pawl 148 engages the next tooth on the ratchet wheel and advances the ratchet wheel clockwise, thereby causing the ratchet wheel to count one mounting, and possibly actuating the release arm as will be described.

It will be appreciated that since the ratchet wheel illustrated has five teeth, it will count five mountings in the way previously described, before the release slot 142 is rotated to a position adjacent the pin 144 on the release arm. Of course, it will be readily understood that by positioning the release slot in a different position with respect to the teeth on the ratchet wheel and/or by increasing and decreasing the number of teeth on the ratchet wheel, the apparatus 20 could release the pin 144 through the release slot upon only one mounting, or upon any number of mountings, as predetermined by the user.

When the pin 144 on the release arm is released through the release slot, the spring 138 urges the release arm to rotate counterclockwise about the first post 30, thereby disengaging the dog 152 on the release arm from the third shelf 218 on the outer cap. When this happens, the compressed streamer 158 forces the outer cap upwardly, thereby disengaging the first and second shelves 214, 216 thereof from the latching ears 28, causing the outer cap to fall free from the inner cap 156, and deploying the streamer to indicate that the animal is in estrus.

As the outer cap falls away from the inner cap, the lanyard 160, which is shorter in length than the streamer, pulls the release pin 208 through the release pin holes 204, 206, thereby releasing the collar 182 on the shaft 172. Referring now to FIGS. 3, 5 and 6, it will be appreciated that the spring 168, which has a length slightly greater than the length of the sleeve 190, urges the shaft 172 towards the small hole 194 in the end of the sleeve 190, the conical depression 232 within the sleeve guiding the shaft to the small hole. The pointed end on the shaft 172 pierces the foil seal 196 thereby initinating release of the fluid 192 contained within the sleeve. It is to be understood that the small hole 194 in the sleeve is sized just slightly larger than the timing shaft so that the fluid within the sleeve is released relatively showly between the shaft and the small hole, under the urging of the spring 168 on the collar 182 of the shaft. Of course, the seal 186 prevents leakage of fluid from the sleeve around the collar on the shaft. It will be appreciated that the shaft will protrude from the end of the sleeve a distance proportional to the amount of fluid released through the small hole 194 around the shaft 172 and thus the distance the shaft protrudes is proportional to the time that has elapsed since the outer cap has fallen away from the inner cap. By suitably selecting the spacing of the graduations 234 on the timing shaft, the viscosity of the fluid 192 within the sleeve, the strength of the spring 168, and the spacing between the shaft 172 and the small hole 194, the shaft can be calibrated to reliably indicate the amount of time that has elapsed. It should be understood that the time it has taken the shaft 172 to protrude any given distance through the small hole 194 will determine the number of seminal ampules required to insure that the cow which the apparatus 20 has indicated as being in estrus will be successfully impregnated. If the release of the outer cover is taken to approximate the end of the final standing mount on the first animal, then the amount of extension of the shaft 172 through the small hole will indicate approximately the time that has elapsed since the final standing mount of that animal.

Applicant turns now to a consideration of the second embodiment of his animal estrus indicating apparatus 236 shown in FIGS. 7–10. It is to be understood that those elements in the apparatus 236 which correspond to those of the apparatus 20, shown in FIGS. 1–6, will be given the same reference numeral, except that a prime is appended i.e., base housing 24 is the same as base housing 24'. The construction and operation of the elements with a prime appended are understood to be the same as their corresponding elements without a prime. It is also to be understood that the outer cap 164' contains an elapsed time indicating mechanism 166', not shown.

Referring now to FIGS. 7–10, it is seen that a fourth post 238 is secured to the base housing 24', as by gluing or molding in one piece with the housing 24'. The no back pawl 74' is secured to the third post 34' as has been previously described. Next, the counting ratchet wheel 116' is assembled to the link arm 114' and the link arm is assembled to the second post 32', as has been previously described, with the bottom collar 124' of the link arm located within the hole through the first gear 240 and spacer 241, and the first gear advance pawl 262 engaging the first gear 240. The lower end of the shaft on the second gear 242 is placed into a first recess 244 in the base housing so that the lower gear 246 thereon meshes with the first gear. The lower end of the shaft on the star gear 248 is placed into a second recess 250 in the base housing such that the lower gear 252 thereof meshes with the upper gear 254 on the second gear. The lower end of the balance arm 256 is placed in the third recess 258 in the base housing with the central portion of balance arm engaging the upper gear 260 on the star gear.

Next, the release arm 134', the release spring 138' and the elastic member 132' are assembled on the first post 30' as has been previously described. Then, the base housing 24', depressible pin 92', spring 90', pressure regulatory mechanism 76' and linkage mechanism 98' are assembled as, has been previously indicated, with one end of the spring 112' being hooked at one end of the link arm 114' as before.

Next, the top plate 264 is secured by passing the top of the first post 30' through both the first post spacer 266 and the first hole 268 in the top plate. Similarly, the top of the second post 32' is padded into the second hole 270 in the top plate, the top of the shaft of the second gear 242 is passed into the third hole 272, the top of the shaft on the star gear 248 is passed into the fourth hole 274, the top of the balance arm 256 is passed into the fifth hole 276, and the top of the fourth post 238 is passed through the sixth hole 278. The top plate is secured in place to the top of the fourth post, as by gluing.

Figure 9:
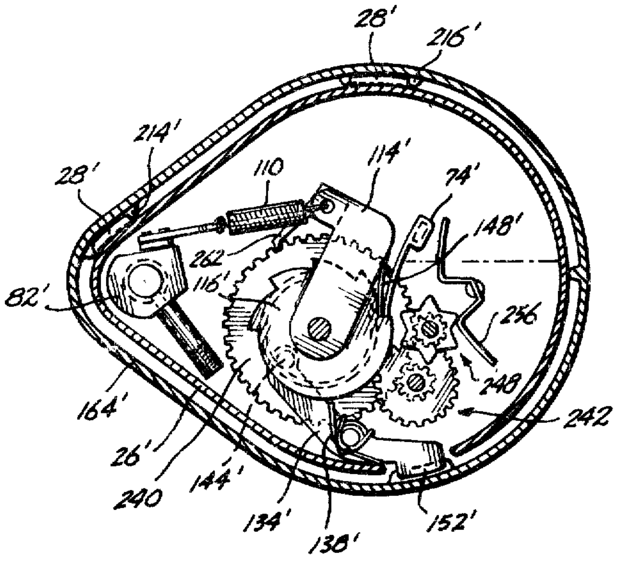
FIG. 9 is a transverse cross section of the embodiment of the present invention shown in FIG. 7 when assembled, prior to release of the release arm.

Then the release arm is cocked and the various elements moved to the positions shown in FIG. 9, in the manner which has been previously described. Next, the inner cap 156' is secured to the base wall 26', one end of the streamer 158' and one of the lanyard 160' are secured to the inner cap, the elements associated with the outer cap 164' are assembled thereto, and the outer cap is secured to the base wall latching ears 28' and the dog on the release arm 152' as has been previously described.

The operation of the embodiment shown in FIGS. 7–10 is identical to that previously described with respect to the embodiment of FIGS. 1–6, except that the release timing mechanism 35, with its four second timing function, is replaced by an escapement type timer 35', as will be now discussed.

As the weight of the second animal mounting the first animal causes the link arm 114' to rotate counterclockwise the first gear advance pawl 262 on the link arm causes the first gear 240 to rotate about the second post 32' in a counterclockwise direction. The rotation of the first gear is transferred through the second gear 242 to the star gear 248 causing it also to rotate counterclockwise, with the upper gear 270 on the star gear causing the balance arm 256 to oscilate. It will be appreciated that the advance pawl 148' on the link arm will not engage the second tooth 230' on the ratchet wheel until a period of, for example, four seconds has elapsed, as determined by the tension of the spring 112' and the sizing and weight of the balance arm 256. Of course, this period of time can be increased or decreased by suitably adjusting the size and weight of balance arm 256, and the gear ratio of the first, second, and star gears 240, 242, 248.

The manner in which the apparatus 236 shown in FIGS. 7–10 counts each mounting, or fails to count a mounting of less than four seconds' duration, the actuation of the release arm 134', the release of the outer cover 164', the deployment of the streamer 158' and the operation of the elapsed time indicating mechanism 166' are as have been previously discussed.

Figure 10:
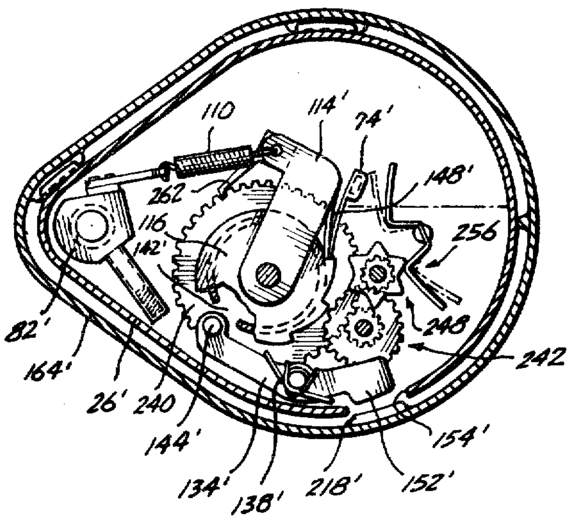
FIG. 10 is a view similar to that of FIG. 9 showing release of the movable release arm.

The position of the various elements of the apparatus 236 at the time of the release of the pin 144' on the release arm 152', and the release of the outer cover 164' by the dog 152' on the release arm is shown in FIG. 10.

Of course, it will be readily understood that by positioning the release slot 142' in a different position with respect to the teeth on the ratchet wheel 116' and/or by increasing and decreasing the number of teeth on the ratchet wheel, the apparatus 236 could release the pin 144' through the release slot upon only one mounting, or upon any number of mountings, as predetermined by the user and as previously discussed with respect to the embodiment 20 shown in FIGS. 1–6.

Of course, it is also to be understood that the release timing mechanisms 35, 35' or could be eliminated, if so desired by the user.

From the foregoing, various further applications, modifications, and adaptations of the apparatus disclosed and the invention embodied therein will now be apparent to those skilled in the art to which the invention is addressed, within the scope of the following claims.

What is claimed is:

1. An apparatus, adapted to be secured to the rump portion of a first animal, for indicating estrus in said first animal, comprising:
   - a base means;
   - a pressure responsive means supported by said base means;
   - a linkage means interconnected with said pressure responsive means;
   - a release means, including a movable release member, interconnected with said linkage means and supported by said base means;
   - a cover means releasably engaged with said base and interconnected with said release means; and
   - an indicating means, mounted on said cover means and wherein
   - said pressure responsive means is for powering said linkage means when said pressure responsive means is subjected to at least a predetermined pressure caused by a second animal mounting said first animal;
   - said linkage means is for powering said release means when said linkage means is powered by said pressure responsive means; and
   - said release means is for releasing said cover means from said base means and actuating said indicating means after said release means has been powered by said linkage means.

2. The apparatus according to claim 1, wherein said pressure responsive means include a depressible member and a pressure regulatory means, interconnected with said depressible member, for determining said predetermined pressure, comprising:

a length of material softer than said depressible member;

a housing means defining a first cavity sized to receive at least a portion of said depressible member, and defining a second cavity, in communication with said first cavity, sized to receive said length of material; and means, interconnected with said housing means, for urging said length of material from said first cavity into said second cavity at a location spaced adjacent one end of said depressible member prior to said predetermined pressure being applied to said depressible member.

3. The apparatus according to claim 1, wherein said indicating means includes an elapsed time timing means for indicating the amount of time that has elapsed since said indicating means has been actuated.

4. The apparatus according to claim 3, wherein:

said elapsed time timing means defines a chamber and a small aperture in communication with said chamber and includes an elapsed time exhibiting means at least partially enclosed by said chamber; and said elapsed time timing means is for releasing a fluid contained in said chamber at a predetermined rate through said small aperture, after said indicating means has been actuated, to expose said elapsed time exhibiting means in an amount proportional to the amount of fluid released through said small aperture.

5. The apparatus according to claim 1, wherein said release means includes a release timing means for preventing said movable release member from actuating said indicating means until said release timing means has been powered by said linkage means for at least a predetermined period of time.

6. The apparatus according to claim 5, wherein said release timing means comprises a timing piston powered by said linkage means, and a timing cylinder which is closed at one end and encloses at least a portion of said timing piston.

7. The apparatus according to claim 5, wherein said release timing means comprises an escapement means powered by said linkage means.

8. The apparatus according to claims 6 or 7, further comprising a counting means, wherein:

said counting means is included in said release timing means and is connected to said movable release member;

said counting means is for counting one count each time said release timing means is powered by said linkage means for said predetermined period of time; and said counting means is for moving said movable release said cover means and actuate member to release said indicating means after said counting means is advanced by said advance means a predetermined number of counts.

9. The apparatus according to claim 8, wherein said indicating means includes an elapsed time timing means for indicating the amount of time that has elapsed since said indicating means has been actuated.

10. The apparatus according to claim 9, wherein:

said elapsed time timing means defines a chamber and a small aperture in communication with said chamber and includes an elapsed time exhibiting means at least partially enclosed by said chamber; and said elapsed time indicating means is for releasing a fluid contained in said chamber at a predetermined rate through said small aperture, after said indicating means has been actuated, to expose said elapsed time recording means in an extent proportional to the amount of fluid released through said small aperture.

11. The apparatus according to claim 10, wherein said pressure responsive means includes a depressible member, and a pressure regulatory means, interconnected with said depressible member, for determining said predetermined pressure comprising:

a length of material softer than said depressible member;

a housing means defining a first cavity sized to receive at least a portion of said depressible member, and defining a second cavity in communication with said first cavity, sized to receive said length of material; and means, interconnected with said housing means, for urging said length of material from said first cavity into said second cavity, at a location spaced adjacent one end of said depressible member, prior to said predetermined pressure being applied to said depressible member.

12. The apparatus according to claim 1, further comprising a counting means, wherein:

said linkage means includes an advance means, connected to said counting means, for advancing said counting means one count each time the linkage means has been powered by said pressure responsive means;

said counting means is included in said release means and is connected to said movable release member; and said counting means is for moving said movable release member to actuate said indicating means after said counting means is advanced by said advance means a predetermined number of counts.

13. The apparatus according to claim 1, wherein said cover means is adapted to pivot relative to said base means when said cover means is subjected to pressure caused by a second animal mounting said first animal to thereby load said pressure responsive means to power said linkage means.

14. The apparatus according to claim 13, wherein said pressure responsive means includes a depressible member in abutting communication with said cover means, and a pressure regulatory means interconnected with said depressible member for determining said predetermined pressure, comprising:

a length of material softer than said depressible member;

a housing means having a first cavity for slidably receiving at least a portion of said depressible member, and a second cavity in communication with said first cavity and sized to receive said length of material; and urging means for urging said length of material from said second cavity into said first cavity at a location adjacent one end of said depressible member.

15. The apparatus according to claim 14, further comprising highly visible, elongate, resilient connecting means interconnecting said base means and said cover means, said connecting means urging said cover means away from said base means when said cover means is released from said base means by said release means.

* * * * *